(12) United States Patent
Stern et al.

(10) Patent No.: US 7,892,218 B2
(45) Date of Patent: Feb. 22, 2011

(54) PH REDUCING FORMULATION

(75) Inventors: Theodor Stern, Jerusalem (IL); Ram Kluger, Pardessea (IL)

(73) Assignee: Rostam Ltd., Caesarea (IL)

( * ) Notice: Subject to any disclaimer, the term of this patent is extended or adjusted under 35 U.S.C. 154(b) by 1136 days.

(21) Appl. No.: 10/791,279

(22) Filed: Mar. 3, 2004

(65) Prior Publication Data

US 2005/0196429 A1 Sep. 8, 2005

(51) Int. Cl.
*A61F 13/15* (2006.01)

(52) U.S. Cl. .................. 604/385.18; 604/904; 424/442

(58) Field of Classification Search ............ 604/385.18, 604/904; 424/442
See application file for complete search history.

(56) References Cited

U.S. PATENT DOCUMENTS

| | | | |
|---|---|---|---|
| 2,201,412 A | 5/1940 | Stein | |
| 4,308,867 A | 1/1982 | Roseman et al. | |
| 4,431,427 A | 2/1984 | Lefren et al. | |
| 4,661,101 A | 4/1987 | Sustmann | |
| 5,374,258 A | 12/1994 | Lloyd et al. | |
| 5,444,113 A * | 8/1995 | Sinclair et al. | 524/306 |
| 5,518,730 A * | 5/1996 | Fuisz | 424/426 |
| 5,993,797 A | 11/1999 | Kitazato et al. | |
| 6,020,453 A | 2/2000 | Larsson et al. | |
| 6,086,909 A | 7/2000 | Harrison et al. | |
| 6,730,057 B2 * | 5/2004 | Zhao et al. | 604/11 |
| 2002/0045873 A1 * | 4/2002 | Kluger et al. | 604/385.18 |
| 2007/0149731 A1 * | 6/2007 | Myers | 526/154 |

FOREIGN PATENT DOCUMENTS

| | | |
|---|---|---|
| WO | WO 91/08726 | 6/1991 |
| WO | 00/59556 | 10/2000 |
| WO | 02/17981 A1 | 3/2002 |
| WO | WO 02/17981 | 3/2002 |

* cited by examiner

*Primary Examiner*—Ardin Marschel
*Assistant Examiner*—Zohreh Vakili
(74) *Attorney, Agent, or Firm*—The Nath Law Group; Susanne M. Hopkins

(57) ABSTRACT

A formulation effective in reducing the pH in a menstruating vagina or in a tampon inserted therein to below pH 5.5, comprising (a) 3-100% by weight of glycolide; (b) optionally 97-15% by weight of a solid organic acid; and (c) optionally 5-30% of a wetting agent. Also disclosed is a catamenial tampon for insertion in a human vagina which comprises the pH reducing formulation.

32 Claims, 6 Drawing Sheets

PH REDUCING FORMULATION

FIELD OF THE INVENTION

This invention relates to an improved pH-reducing formulation, and a tampon comprising the same.

BACKGROUND OF THE INVENTION

The normal, healthy human vagina is weakly acidic and has a pH of approximately 4.5. This acidic condition of the vagina provides an effective barrier against the growth of pathogenic microorganisms normally associated with vaginal infection, because such microorganisms do not grow below a pH of about 5. If, however, the pH of the vagina becomes less acidic, i.e., higher than about 5, pathogenic microorganisms tend to multiply.

A change in pH of the vagina from the normal of about 4.5 to 5 to a more alkaline pH may be brought about by various vaginal conditions and may occur at any time during the menstrual cycle. During menstruation, in particular, the vagina becomes less acidic due to the presence of menstrual fluid which has a pH of from about 7 to 8. As a result, the protective barrier provided by the normal acidic condition of the vagina becomes less effective, thereby providing an environment favorable to the growth of the pathogenic microorganisms.

To overcome the reduction in acidity of the vagina and to re-establish the desired normal acidic condition, different formulations and techniques have been developed. Such efforts have included the development of formulations such as solutions, jellies, powders, suppositories, and the like containing acidifying materials which are introduced into the vagina in their prepared form.

While the above-mentioned types of products have met with acceptance, they are subject to numerous disadvantages. The solutions, jellies, powders, and suppositories containing acidifying materials may be inconvenient to handle and apply and are not fully retained in the vagina and tend to leak. In addition, they do not have capacity for absorbing vaginal fluid which may be present in the vagina, particularly during menstruation. Therefore, to use such products during menstruation, it is also necessary to use at the same time a catamenial tampon or similar article.

Other attempts to lower the pH have included physically incorporating acidifying materials into absorbent products by coating, spraying, impregnating and the like, to impart to such products acidifying properties.

U.S. Pat. No. 4,431,427 to Lefren et al, discloses a tampon having incorporated therein one or more organic acids in combination with at least one of oligomer and polymer derivatives of the acids. The acids may be citric, gylcolic, malic, tartaric or lactic acids. The tampon is intended for maintaining a pH of about 4.5 to 2.5 in the fluids absorbed by the tampon during use, thereby inhibiting the growth of pathogenic bacteria in the tampon.

U.S. Pat. No. 4,661,101 to Sustmann discloses a catamenial tampon comprising a microbistatic fibrous absorbant core and an outer covering layer of a pH-regulating fibrous, cellulose material. The cellulose fibers are modified by carboxymethyl groups which are converted into their free acid form by treatment with an acid.

WO 91/08726 discloses a disposable sanitary napkin comprising a water permeable topsheet, an absorbent core and a water impermeable backsheet. The topsheet and/or backsheet comprise absorbable, hydrolyzable and biodegradable substances such as a lactic acid-based or glycolic acid-based polyester. This enhances the disposability of the napkin.

U.S. Pat. No. 6,020,453 to Larsson et al, discloses an absorbent article having a surface material, wherein the surface material includes a surface layer (being the outermost layer) which comprises a lactic acid-based polyester. The surface material is capable of excreting lactic acid to the surrounding urogenital region of menstruating women so as to establish a pH value of at most 4.0. The polyester has a molecular weight of at most 50,000 and the monomer/oligomer concentration is 5-30% by weight.

WO 02/17981 and U.S. 2002/0045873 discloses a formulation effective in reducing the pH in a menstruating vagina or in a tampon inserted therein to below pH 5.5 comprising: (a) 3-80% by weight of a solid organic acid polymer; (b) 92-15% by weight of a solid organic acid; and (c) 5-30% of a wetting agent. In a preferred embodiment, the organic acid polymer is a polymer of lactic acid. Preferred polymers are L-lactide or DL-lactide (LD), a racemic mixture of a cyclic dimer of lactic acid, and polylactic acid (PLA) in the general range of 200-2000 MW.

Glycolide is a cyclic dimer of glycolic acid, containing two ester groups which upon contact with an aqueous environment are hydrolyzed, resulting in two glycolic acid molecules.

SUMMARY OF THE INVENTION

It is an object of the present invention to provide a novel formulation capable of reducing the pH in the menstruating vagina and/or in the tampon.

It is a further object of the invention to provide a feminine hygienic product, such as a tampon, containing the novel formulation.

In a first aspect, the present invention provides a formulation effective in reducing the pH in a menstruating vagina or in a tampon inserted therein to below pH 5.5 comprising: (a) 3-100% by weight of glycolide; (b) optionally, 97-15% by weight of a solid organic acid; and/or (c) optionally, 5-30% of a wetting agent.

In a further embodiment, the formulation can also include lactide. In additional embodiments the solid organic acid can be citric, malic, maleic, fumaric, succinic, tartaric, glycolic and oxalic acids and the wetting agent can be glycerol, polyethylene glycol (PEG), polypropylene glycol (PPG), Tween 80™, Poloxamer™ (Pluronic) and surfactants with an HLB ranging from 10 to 18. A preferred solid organic acid is citric acid and preferred wetting agents are glycerol and PEG-8000.

In a second aspect, the invention provides a catamenial tampon for insertion in a human vagina comprising the formulation of the invention. The formulation may be placed directly on the tampon, or indirectly, e.g. on a strip as described in WO 02/17981 and U.S. 2002/0045873, and as described below.

Other features and advantages of the invention will be apparent from the following detailed description and claims.

BRIEF DESCRIPTION OF THE DRAWINGS

In order to understand the invention and to see how it may be carried out in practice, some embodiments will now be described, by way of non-limiting example only, with reference to the accompanying drawings in which.

DETAILED DESCRIPTION OF THE INVENTION

Figure 1:
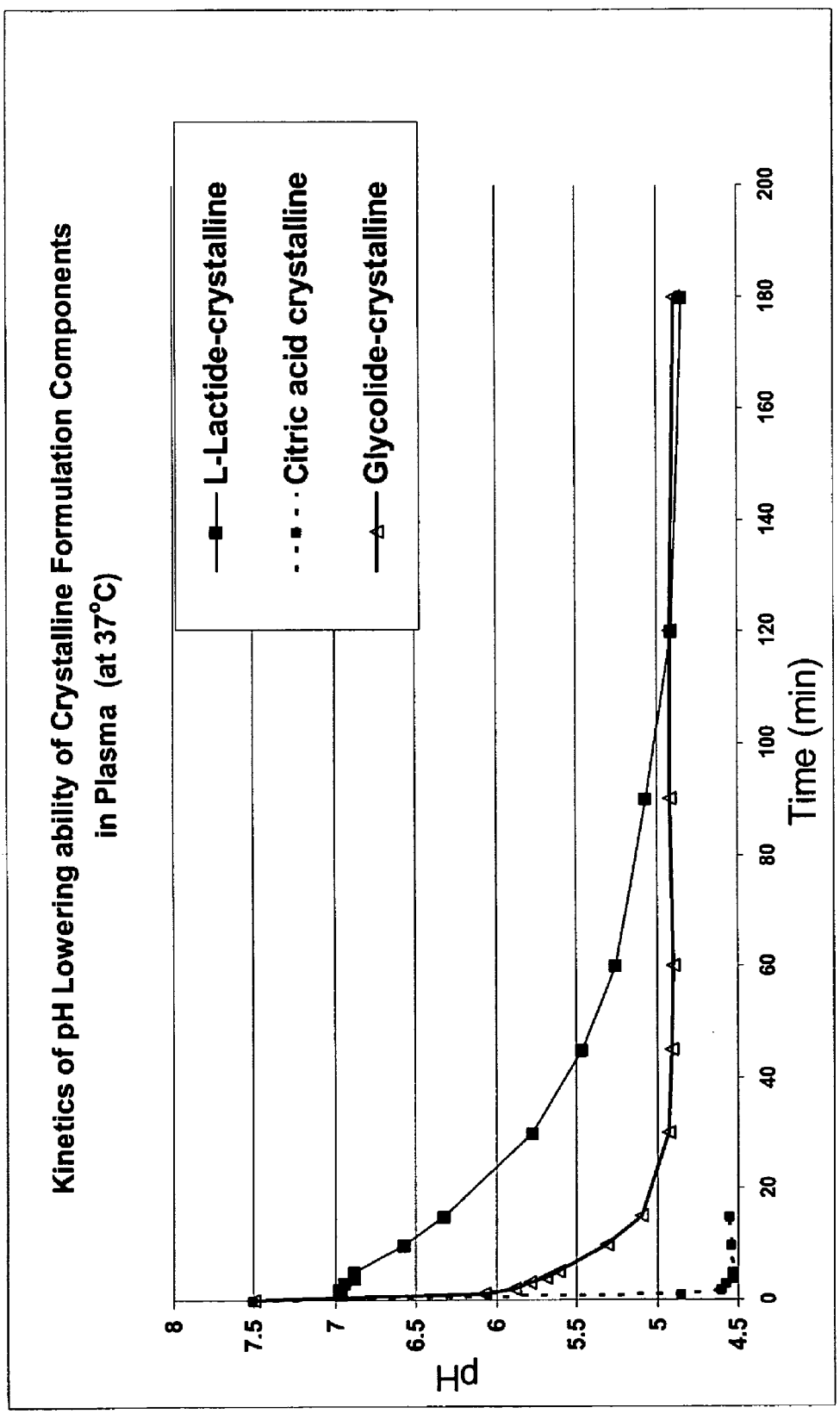
FIG. 1 is a line graph illustrating the kinetics of pH lowering ability of L-lactide, glycolide and citric acid, in crystalline form, in plasma at 37° C.

It is an object of the present invention to provide a novel formulation capable of reducing the pH in the menstruating vagina and/or in the tampon. It is a further object of the invention to provide a feminine hygienic product, such as a tampon, containing the novel formulation.

In a first aspect, the present invention provides a formulation effective in reducing the pH in a menstruating vagina or in a tampon inserted therein to below pH 5.5 comprising: (a) 3-100% by weight of glycolide; (b) optionally, 97-15% by weight of a solid organic acid; and/or (c) optionally, 5-30% of a wetting agent. In a further embodiment, the formulation also includes lactide.

Thus, the invention includes the following formulations:
glycolide alone;
glycolide+lactide;
glycolide+solid organic acid;
glycolide+lactide+solid organic acid
glycolide+wetting agent;
glycolide+lactide+wetting agent;
glycolide+solid organic acid+wetting agent; and
glycolide+lactide+solid organic acid+wetting agent.

The glycolide of the formulation includes two glycolic acid monomers and is primarily non-acidic prior to hydrolysis. The glycolide comprises 3-100% of the formulation, with a preferred lower boundary of 30%, most preferably 50%, and a preferred upper boundary of 90%, most preferably 80%.

Lactide if present in the formulation can comprise 3-97% of the formulation, with a preferred lower boundary of 15%, most preferably 30%, and a preferred upper boundary of 60%, most preferably 50%. Lactide can be L-lactide or DL-lactide (LD).

Examples of solid organic acids are citric, malic, maleic, fumaric, succinic, tartaric, glycolic and oxalic acids. A preferred organic acid is citric acid. The organic acid comprises (when present) 97-15% of the formulation, and preferably 30-15%.

Examples of wetting agents which may be used in the formulation of the invention include glycerol, polyethylene glycol (PEG), polypropylene glycol (PPG), Tween 80™, Poloxamer™ (Pluronic) and surfactants with an HLB ranging from 10 to 18. Preferred wetting agents are glycerol and PEG-8000. The wetting agent comprises (when present) 5-30% of the formulation, and preferably 5-10%.

The formulation may comprise additional substances such as stabilizers, perfuming agents, preservatives, anti-oxidants, chelating agents, adsorbents, analgesic agents, anti-inflammatory agents, etc.

The kinetics and efficacy of the pH lowering process can be tailored by changing the formulation amount, composition and ingredients ratio as will be readily understood by the skilled man of the art. In this context, the combined use of lactide, glycolide, citric acid and glycerol, as the pH tampon formulation, will provide effective acid release within the tampon-use timeframe. Nevertheless, as shown in the preliminary results presented below, the special properties of glycolide offer the possibility of using it both alone and in combination with other pH lowering agents. Also, as shown below, glycolide does not require the use of a wetting agent (e.g. glycerol) in order to significantly improve the short and medium term release profile, as is not the case with lactide.

In a second aspect, the invention provides a catamenial tampon for insertion in a human vagina comprising the formulation of the invention. The formulation may be placed directly on the tampon, or indirectly, e.g. on a strip as described in WO 02/17981 and U.S. 2002/0045873, and as described below.

The invention is further defined by reference to the following examples. It is understood that the foregoing detailed description and the following examples are illustrative only and are not to be taken as limitations upon the scope of the invention. It will be apparent to those skilled in the art that many modifications, both to the materials and methods, may be practiced without departing from the purpose and interest of the invention. Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In the case of conflict, the present specification, including definitions, will control.

EXAMPLES

The pH lowering ability of glycolide in its crystalline form, obtained from Purac Ltd., Holland, was tested in plasma at 37° C. as a function of time, compared to that of lactide and citric acid (also in crystalline form). All three materials were taken such as to eventually yield equal molar amounts of carboxylic acid groups.

The results are presented in FIG. 1 and show surprisingly that the degradation process of glycolide is significantly faster than that of lactide. The degradation of glycolide was completed in approximately 40 minutes, while the degradation of lactide was completed in approximately 120 minutes. Nevertheless, the degradation of glycolide and thus, the release of glycolic acid is much slower than the burst-like immediate release of the citric acid.

Figure 2:
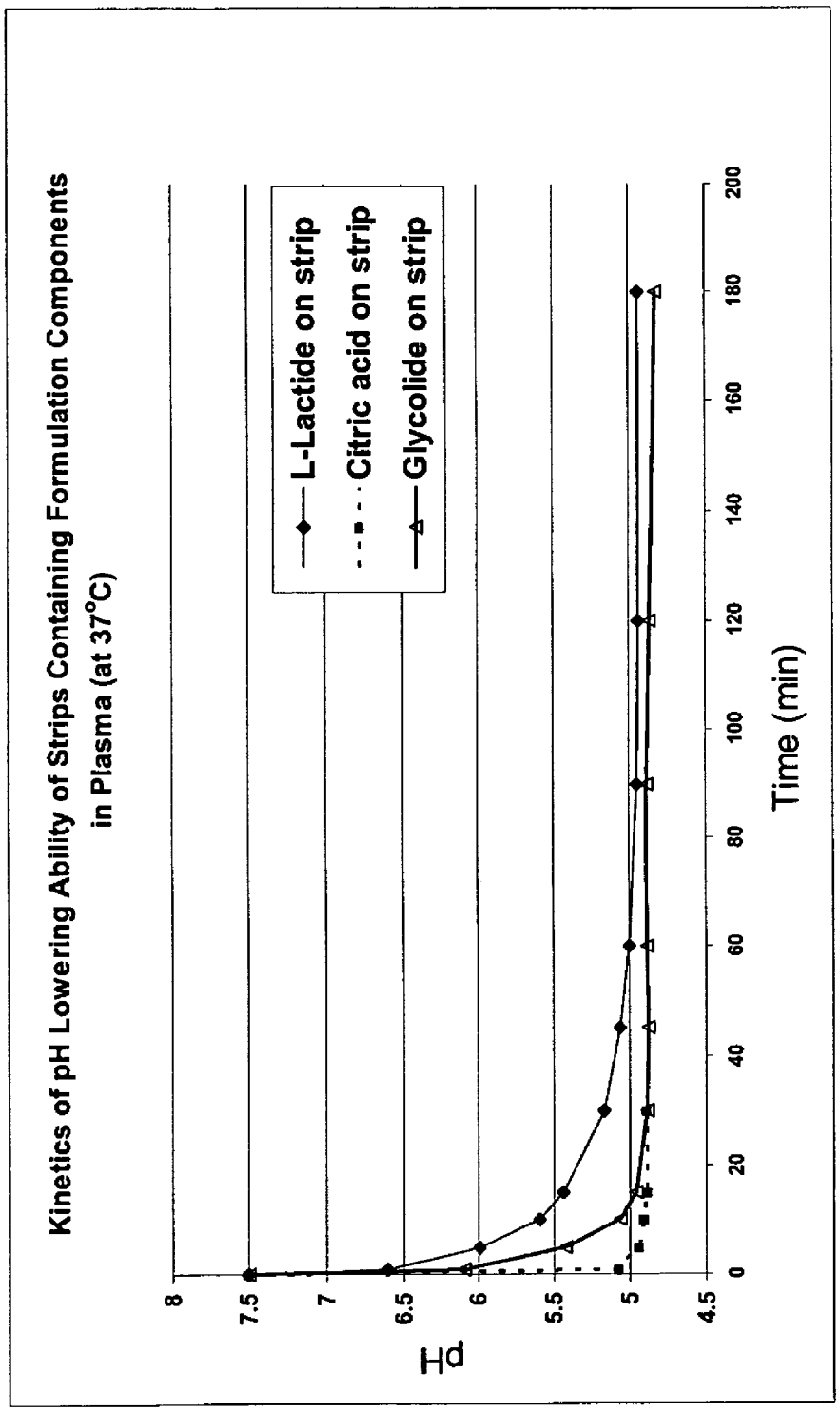
FIG. 2 is a line graph illustrating the kinetics of pH lowering ability of non-woven strips containing L-lactide, glycolide and citric acid, in plasma at 37° C.

The same experiment was repeated by comparing the pH lowering kinetics of the same compounds, deposited onto a polymeric support in the form of weighed (240 mg), rectangular shaped pieces of non-woven (NW) tampon cloth (hereinafter referred to as "strips") by evaporation from an acetone solution, substantially as described in WO 02/17981 and U.S. 2002/0045873 whose contents are hereby incorporated by reference in their entireties. The strips may be incorporated in a tampon. The strips were dipped in plasma at 37° C. The results presented in FIG. 2 show a two-fold increase in the degradation rate of both lactide and glycolide when deposited on the strips. This change in the degradation rates most probably stems from the essentially amorphous state of the compounds obtained through the deposition process. Still, the relative difference between the two compounds is maintained and both are significantly different from citric acid, which behaved as previously described.

As stated above, WO 02/17981 and U.S. 2002/0045873 disclose a pH reducing formulation in a tampon comprising a combination of lactide and citric acid as active agents. This combination is advantageous by offering both a short and long-term pH regulating activity, the citric acid component being released before significant degradation of lactide takes place. Also, a wetting agent such as glycerol was added in order to promote the access of water molecules to the relatively hydrophobic lactide. The same concept was applied with glycolide with surprising and improved results.

The pH lowering effect of tampons containing non-woven strips loaded with glycolide in two different formulations, was tested as a function of incubation time and plasma volume. The tampons were placed at 37° C. in a device (named "SYNGINA"), recommended by the US FDA to simulate the lateral pressure acting on the tampon under natural conditions. Thus, the wetting profile inside the tampon would resemble the natural conditions as closely as possible. Human plasma was added dropwise at a rate of 1 ml/h. The pH obtained with tampons containing glycolide alone and in combination with citric acid (CA) and/or glycerol, and lactide with CA and glycerol, was measured by extracting the released acids from the tampons with 75 ml of distilled water after incubation with plasma in the SYNGINA device at 37° C. The extraction time was restricted to 30 seconds, in order to prevent further lactide or glycolide degradation during the extraction process.

Figure 3:
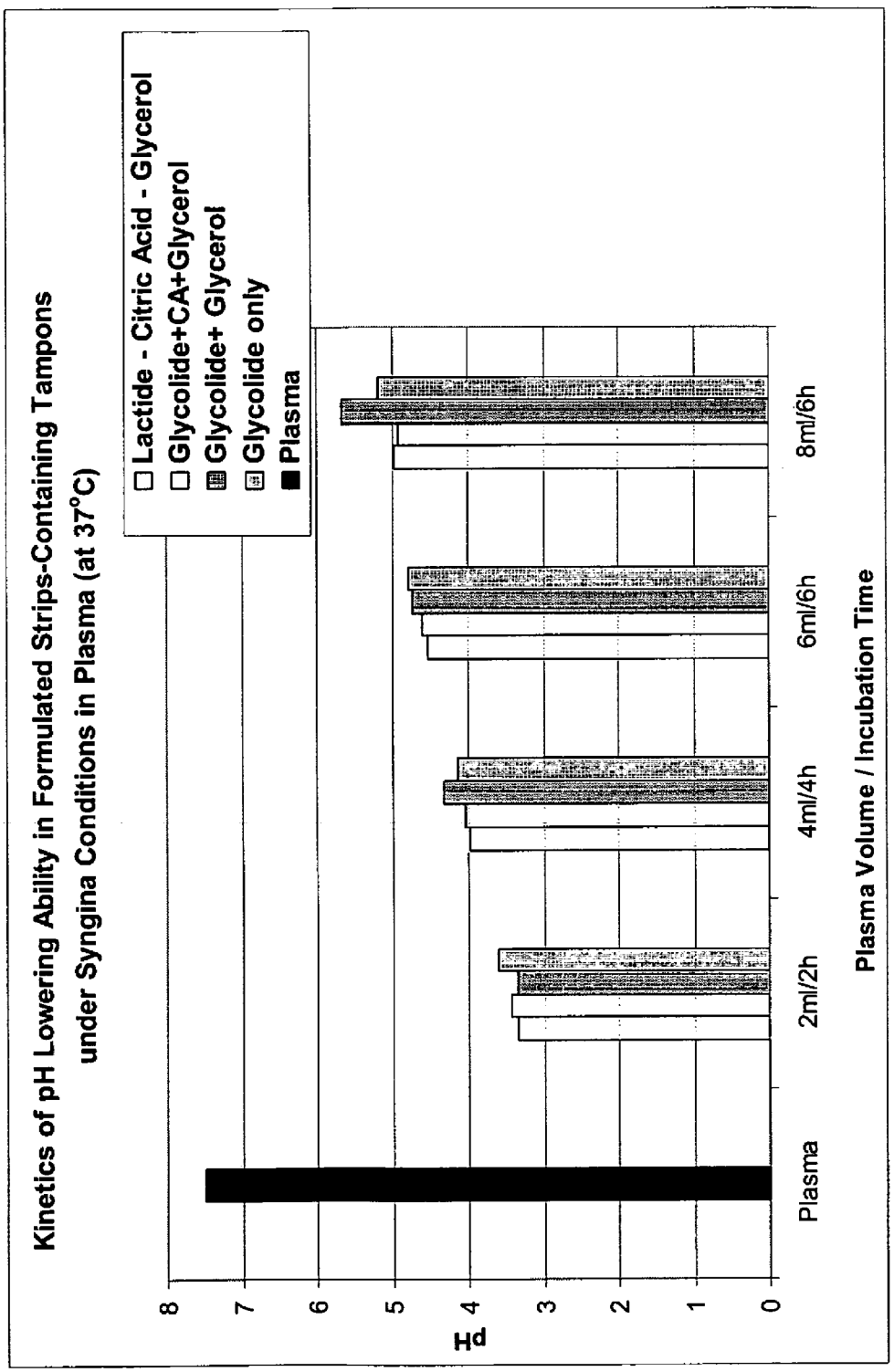
FIG. 3 is a bar graph illustrating the pH lowering effect of tampons containing formulated non-woven strips with glycolide alone; glycolide and glycerol; glycolide with citric acid and glycerol; and lactide with citric acid and glycerol, under SYNGINA conditions, using plasma at 37°0 C.

The results are described in FIG. 3 which shows the pH lowering effects of glycolide and indicates that glycolide can replace lactide in the formulation comprising cyclic dimer, CA and glycerol.

Figure 4:
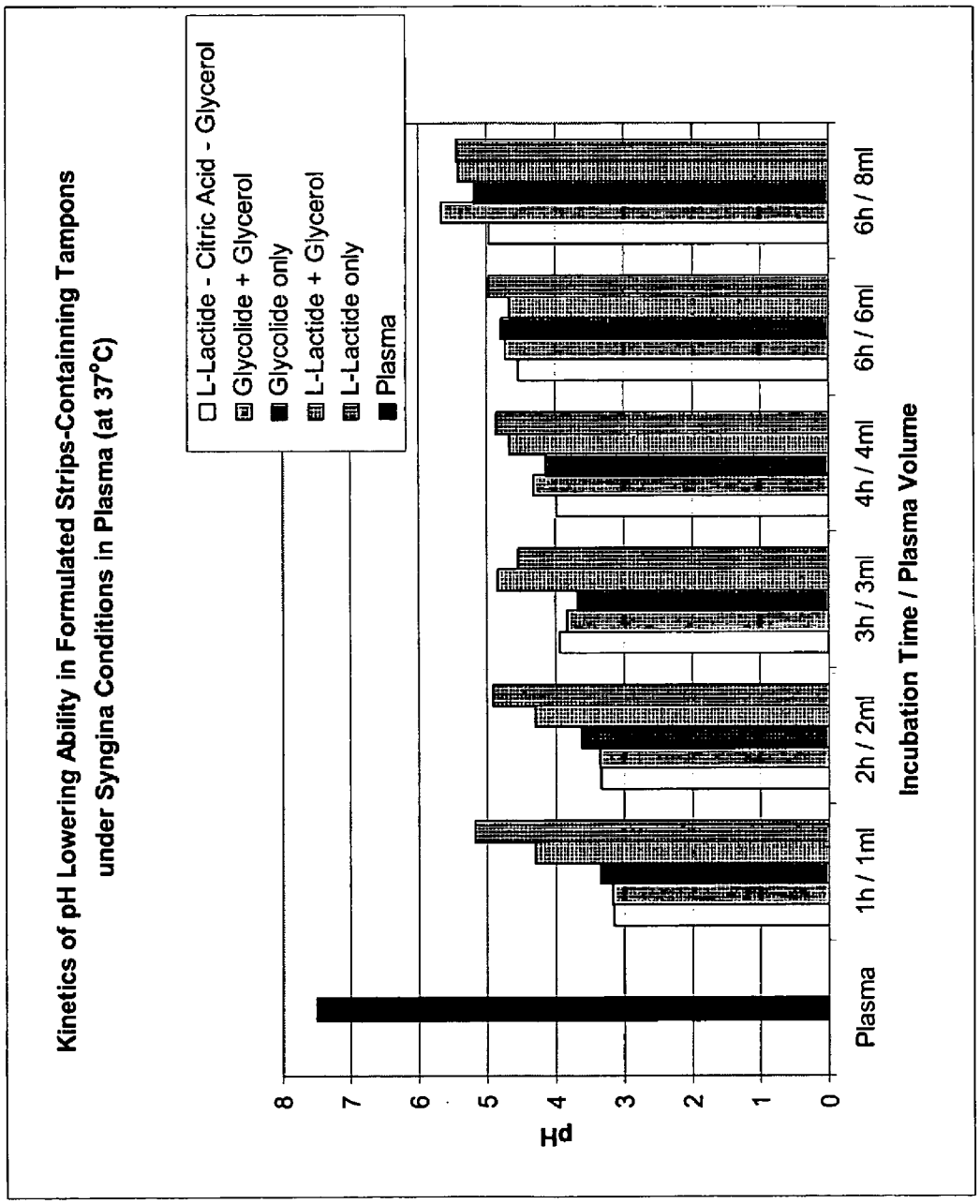
FIG. 4 is a bar graph illustrating the pH lowering effect of tampons containing formulated non-woven strips with lactide alone; lactide and glycerol; lactide with citric acid and glycerol; glycolide alone; and glycolide with glycerol, under SYNGINA conditions, using plasma at 37° C.

The pH lowering ability of lactide and glycolide, with and without wetting agent (glycerol)—on strips in tampons—as a function of plasma volume and incubation time in SYNGINA, was compared to the previously disclosed pH formulated tampon (lactide, citric acid and glycerol). The results are shown in FIG. 4. The presence of glycerol (wetting agent) significantly improves the pH lowering ability of lactide during the first two hours. This effect is very small when using glycolide. Thus, the pH lowering efficacy of glycolide alone is very similar to that of glycolide combined with the wetting agent (glycerol). Hence, one of the advantages in using glycolide is the reduced necessity of using a wetting agent in terms of improving degradation and release kinetics. Moreover, during the first 4 hours the results obtained using glycolide were very similar to those obtained with the previously disclosed pH formulation. It thus may be seen that by replacing lactide with glycolide, the necessity of adding an organic acid and/or wetting agent is diminished or eliminated.

Figure 5:
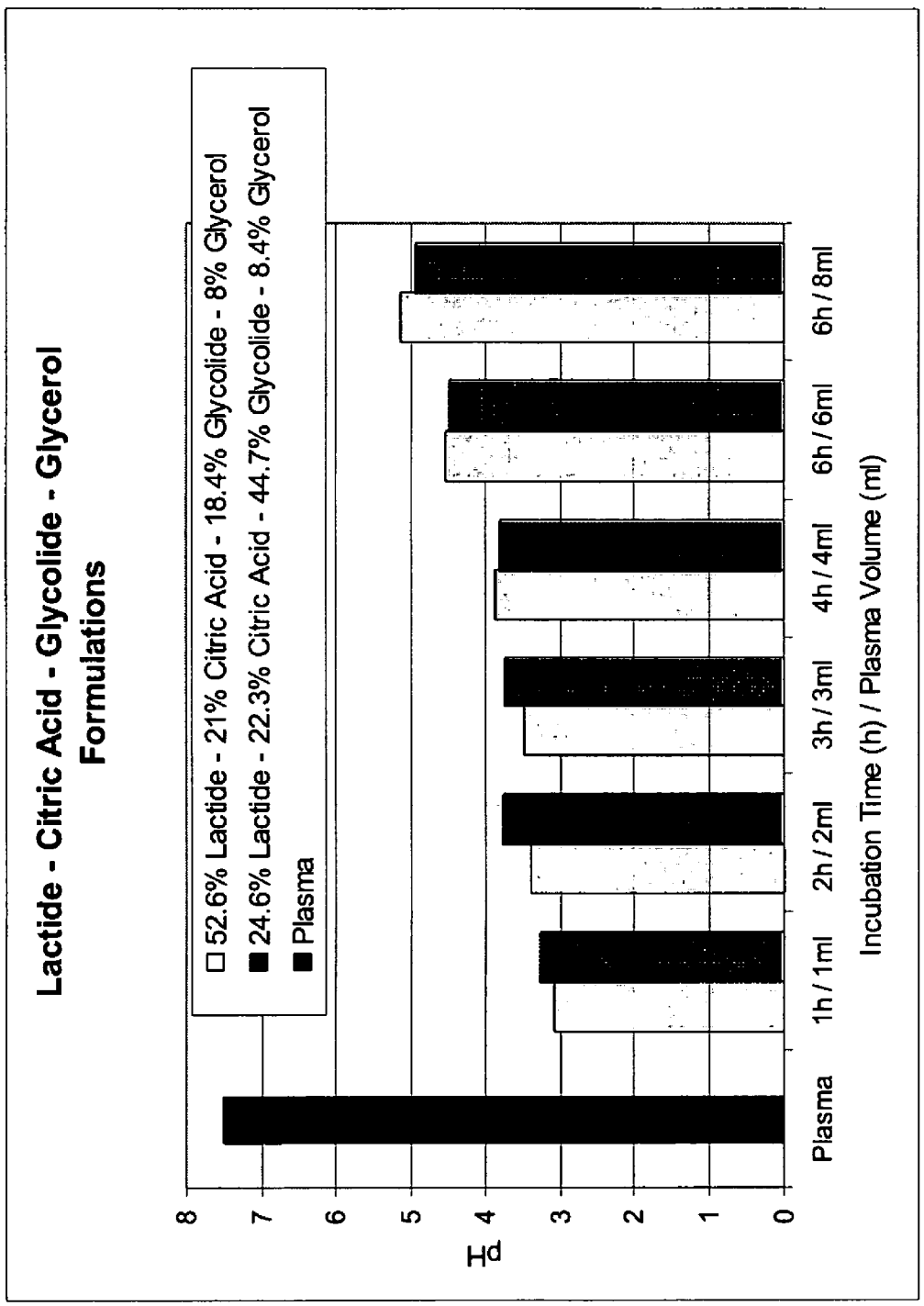
FIG. 5 is a bar graph illustrating the pH lowering effect of tampons containing formulated non-woven strips with lactide, glycolide, citric acid and glycerol (at two different weight ratios of lactide and glycolide as indicated in the graph, but having the same total molar amount of carboxyl groups), under SYNGINA conditions, using plasma at 37° C.

The combined use of lactide, glycolide and citric acid as the pH formulation for a tampon, provides the advantage of using three different formulation ingredients exhibiting relatively slow, medium and fast release kinetics, respectively. A wetting agent (e.g. glycerol) may be used to enhance the release kinetics of lactide. FIG. 5 exhibits the results obtained with tampons containing such a triple component formulation, with the addition of glycerol, under SYNGINA conditions. It can be seen that a range of component weight percentages may be used.

Figure 6:
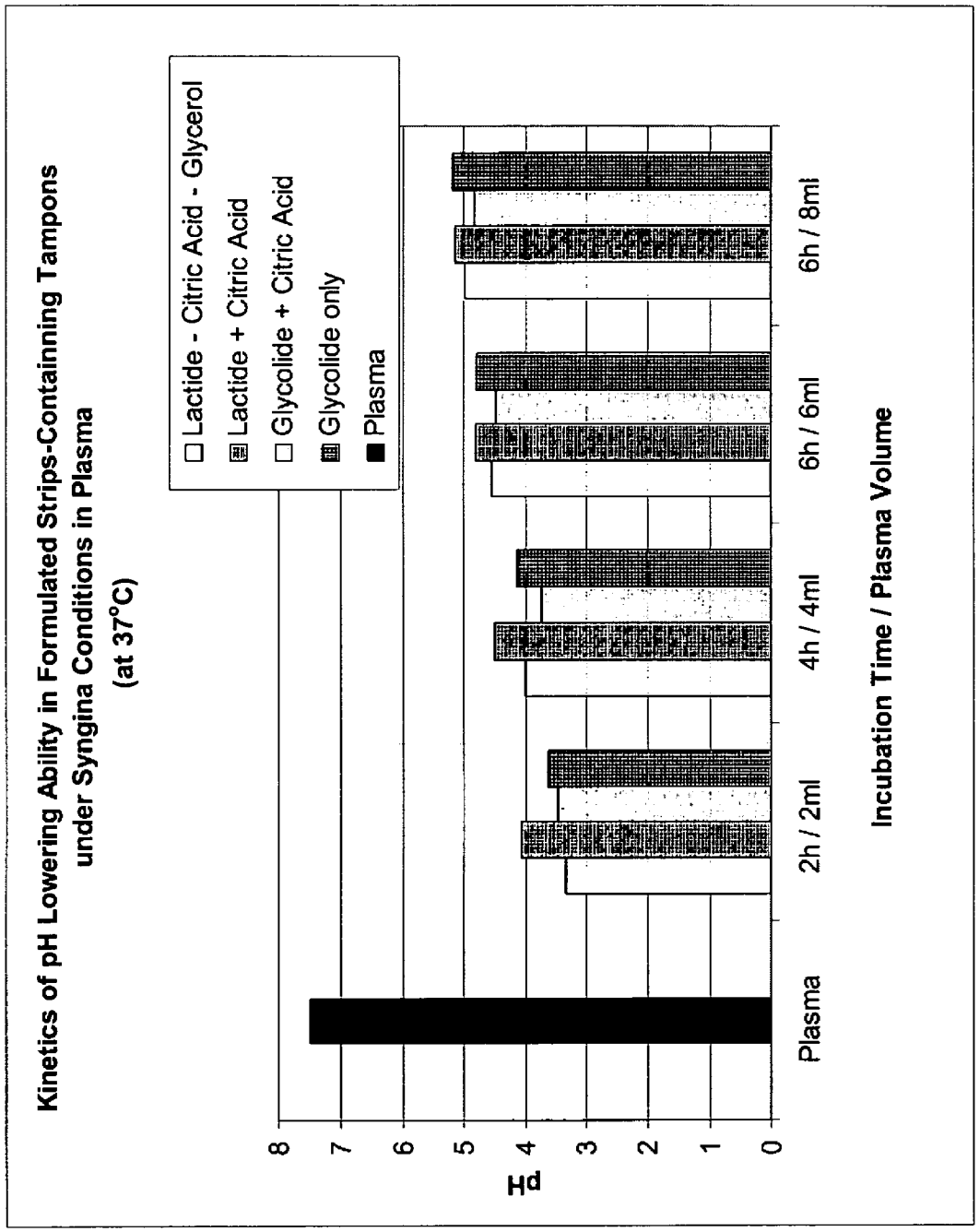
FIG. 6 is a bar graph illustrating the pH lowering effect of tampons containing formulated non-woven strips with lactide, citric acid and glycerol; lactide and citric acid; glycolide and citric acid; and glycolide alone (having the same total molar amount of carboxyl groups), under SYNGINA conditions, using plasma at 37° C.

The results presented in FIG. 6, indicate that the combination of glycolide and citric acid is consistently more efficacious than the lactide-citric acid combination, again indicating that without the presence of a wetting agent, glycolide degrades quicker than lactide. The pH lowering kinetics of glycolide alone is slightly slower than that of the glycolide-citric acid combination, due to the presence of the readily available free acid in the latter formulation. The combination of lactide, citric acid and glycerol (wetting agent) is about as efficacious as the glycolide-citric acid formulation, again indicating the improving effect of the wetting agent on the degradation kinetics of the more hydrophobic lactide.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A catamenial tampon for insertion in a human vagina, comprising:
   (a) an inner core comprising an absorbent material;
   (b) an outer layer comprising a liquid permeable material; and
   (c) a formulation effective in reducing the pH in a menstruating vagina or in a tampon inserted therein to below pH 5.5, the formulation comprising
   30-100 wt % of glycolide; wherein glycolide is a cyclic dimer of glycolic acid,
   optionally, 15-97 wt % of a solid organic acid; and
   optionally, 5-30 wt % of a wetting agent, based on the total weight of the formulation.

2. The catamenial tampon according to claim 1, the formulation further comprising lactide.

3. The catamenial tampon according to claim 2, wherein lactide is present in the formulation in an amount of from 3 to 97 wt % based on the total weight of the formulation.

4. The catamenial tampon according to claim 1, wherein glycolide is present in the formulation in an amount of from 30 to 80 wt % based on the total weight of the formulation.

5. The catamenial tampon according to claim 1, wherein the formulation comprises the solid organic acid.

6. The catamenial tampon according to claim 5, wherein the solid organic acid is present in the formulation in an amount of from 15 to 30 wt % based on the total weight of the formulation.

7. The catamenial tampon according to claim 5, wherein the solid organic acid is selected from the group consisting of citric, malic, maleic, fumaric, succinic, tartaric, glycolic and oxalic acids.

8. The catamenial tampon according to claim 1, wherein glycolide is present in the formulation in an amount of 100 wt % based on the total weight of the formulation.

9. The catamenial tampon according to claim 1, wherein the formulation comprises a wetting agent in an amount of from 5 to 10 wt % based on the total weight of the formulation.

10. The catamenial tampon according to claim 1, wherein the wetting agent is selected from the group consisting of glycerol, polyethylene glycol (PEG), polypropylene glycol (PPG), Tween 80™, Poloxamer™ (Pluronic) and surfactants with an HLB ranging from 10 to 18.

11. The catamenial tampon of claim 1, wherein upon insertion of the catamenial tampon in a menstruating vagina the pH in the menstruating vagina or in the tampon is reduced to below 5.5 within about one hour or less from the time of insertion.

12. The catamenial tampon of claim 1, wherein upon insertion of the catamenial tampon in a menstruating vagina the pH in the menstruating vagina or in the tampon is reduced to below 5.5 within about 20 minutes or less from the time of insertion.

13. The catamenial tampon of claim 1, wherein upon insertion of the catamenial tampon in a menstruating vagina the pH in the menstruating vagina or in the tampon is reduced to below 5.5 within about 10 minutes or less from the time of insertion.

14. The catamenial tampon of claim 1, further comprising a polymeric support provided between the inner core and the outer layer.

15. The catamenial tampon of claim 14, wherein the formulation is deposited on the polymeric support.

16. The catamenial tampon of claim 1, wherein the catamenial tampon does not contain lactide, an organic acid, and/or a wetting agent.

17. The catamenial tampon of claim 1, wherein the catamenial tampon does not contain lactide, an organic acid, and a wetting agent.

18. The catamenial tampon of claim 17, further comprising a polymeric support provided between the inner core and the outer layer.

19. The catamenial tampon of claim 18, wherein the formulation is deposited on the polymeric support.

20. A method for reducing the pH in a menstruating vagina to below pH 5.5, comprising inserting into the vagina, a catamenial tampon according to claim 17.

21. The method of claim 20, wherein after inserting, pH in the menstruating vagina is reduced to below pH 5.5 within one hour or less from the time of insertion.

22. A catamenial tampon for insertion in a human vagina, comprising:
    (a) an inner core comprising an absorbent material;
    (b) an outer layer comprising a liquid permeable material; and
    (c) a formulation effective in reducing the pH in a menstruating vagina or in a tampon inserted therein to below pH 5.5, the formulation comprising
    30-100 wt % of glycolide; wherein glycolide is a cyclic dimer of glycolic acid,
    optionally, 15-97 wt % of a solid organic acid; and
    optionally, 5-30 wt % of a wetting agent, based on the total weight of the formulation.

23. The catamenial tampon of claim 22, wherein the formulation further comprises lactide.

24. The catamenial tampon of claim 22, wherein the formulation comprises 100 wt % glycolide, and the catamenial tampon does not contain lactide, an organic acid and a wetting agent.

25. A catamenial tampon for insertion in a human vagina, comprising:
    (a) an inner core comprising an absorbent material;
    (b) an outer layer comprising a liquid permeable material; and
    (c) a formulation effective in reducing the pH in a menstruating vagina or in a tampon inserted therein to below pH 5.5, the formulation comprising
    30-100 wt % of glycolide; wherein glycolide is a cyclic dimer of glycolic acid,
    optionally, 15-97 wt % of a solid organic acid; and
    optionally, 5-30 wt % of a wetting agent, based on the total weight of the formulation.

26. The catamenial tampon of claim 25, wherein upon insertion of the catamenial tampon in a menstruating vagina the pH in the menstruating vagina or in the tampon is reduced to below 5.5 within about one hour or less from the time of insertion.

27. The catamenial tampon of claim 25, wherein upon insertion of the catamenial tampon in a menstruating vagina the pH in the menstruating vagina or in the tampon is reduced to below 5.5 within about 20 minutes or less from the time of insertion.

28. The catamenial tampon of claim 25, wherein upon insertion of the catamenial tampon in a menstruating vagina the pH in the menstruating vagina or in the tampon is reduced to below 5.5 within about 10 minutes or less from the time of insertion.

29. The catamenial tampon of claim 25, wherein the catamenial tampon does not contain lactide.

30. The catamenial tampon of claim 25, wherein the catamenial tampon does not contain lactide, an organic acid, and a wetting agent.

31. The catamenial tampon of claim 25, wherein the polymeric support comprises at least one strip having one or more layers.

32. The catamenial tampon of claim 31, wherein the polymeric support comprises more than one strip, each strip having one or more layers.

* * * * *